United States Patent [19]

Forgues et al.

[11] Patent Number: 4,794,647
[45] Date of Patent: Dec. 27, 1988

[54] AUTOMATIC OPTICAL INSPECTION SYSTEM

[75] Inventors: Pierre M. Forgues, Greenfield Park; Birendra Prasada, Westmount, both of Canada

[73] Assignee: Northern Telecom Limited, Montreal, Canada

[21] Appl. No.: 721,016

[22] Filed: Apr. 8, 1985

[51] Int. Cl.[4] .................................................. G06K 9/00
[52] U.S. Cl. .................................... 382/8; 358/106; 382/36
[58] Field of Search ................ 356/237; 382/8, 36, 382/34, 35, 30; 358/106

[56] References Cited

U.S. PATENT DOCUMENTS

| | | | |
|---|---|---|---|
| 4,223,387 | 9/1980 | Danielsson | 382/8 |
| 4,345,312 | 8/1982 | Yasuye | 382/8 |
| 4,377,238 | 3/1983 | Wilks et al. | 358/106 |
| 4,441,207 | 4/1984 | Lougheed | 382/27 |
| 4,500,202 | 2/1985 | Smyth | 382/8 |
| 4,578,810 | 3/1986 | MacFarlane | 358/106 |
| 4,589,140 | 5/1986 | Bishop | 382/27 |
| 4,628,531 | 12/1986 | Okamoto | 356/237 |
| 4,668,982 | 5/1987 | Tinnerino | 358/106 |
| 4,692,943 | 9/1987 | Pietzsch | 358/106 |

Primary Examiner—Leo H. Boudreau
Assistant Examiner—Joseph Mancuso
Attorney, Agent, or Firm—Thomas Adams

[57] ABSTRACT

An automatic optical inspection system, for inspecting printed circuit boards and the like, employs so-called dimensional verification and pattern recognition techniques simultaneously. The printed circuit board is scanned by means of a CCD camera to produce a binarized image of the board. The image is stored and access provided to a set of picture elements arranged in a generally circular configuration and which are spaced apart by a dimension to be monitored by dimensional verification (DV) means. Access is also provided to a second set of picture elements arranged in a generally rectangular array of picture elements for the pattern recognition (PR) means, which uses template matching to determine their validity. The DV and PR outputs are weighted and clustered before a fault is signalled.

38 Claims, 8 Drawing Sheets

CELL ARRAY 1: 4×6
CELL ARRAY 2: 3×5

AUTOMATIC OPTICAL INSPECTION SYSTEM

The invention relates to automatic inspection systems, especially for inspecting articles such as photomasks for maiing printed circuit boards (PCBs) or semiconductor devices, the circuit boards or semiconductor devices themselves (particularly interconnection patterns of integrated circuits), and like articles having a pattern of lines of predetermined configuration.

Generally, known automatic optical inspection systems comprise means for acquiring an image of the article being inspected, the acquired image usually being represented digitally, and processing means for evaluating the image to determine whether or not the article is defective. In some systems the image-acquisition means comprises an array of sensors, for example CCD sensors, arranged to receive radiation transmitted through or reflected from the article from a remote source. The article is scanned, conveniently by moving it across a row of the sensors and scanning the sensors electronically. The analogue outputs of the sensors, which are proportional to light intensity, are then digitized and bilevel coded.

A typical such scanning system is disclosed by W. M. Sterling in a paper entitled "Automatic Non-reference Inspection of Printed Wiring Boards", Proc. PRIP79-Computer Soc. on Pattern Recognition and Image Processing, 1979 pp 93-100.

An alternative scanning system, wherein a stationary article is scanned by a laser beam, is disclosed by R. C. Restrick in a paper entitled "An Automatic Optical Printed Circuit Inspection System", SPIE Vol. 116, Solid State Imaging Devices, 1977.

The Processing of the image data is then usually done by either of two procedures depending upon whether the system is of the "reference" or "non-reference/local" kind. Reference systems compare the pattern of the entire article with a reference template obtained from, for example, computer-aided design (CAD) data or a master or reference article. Such reference systems are not entirely satisfactory because, when micrometer resolutions are involved, it is difficult and time-consuming to align the respective images of the template and the article being inspected, whether this is done physically or by signal processing.

In non-reference systems, only a small area of the article is examined at any particular time and such examination is for local consistency with predetermined design rules or characteristics. In the case of, for example, a PCB photomask created using CAD, the design rules will be specific and relatively few in number. For example, line orientation might be limited to orthogonal and 45° thereto, and pads to rectangular (usually square) or elliptical uusually circular). Lines also would have constant width and at least a prescribed minimum spacing between them. Accordingly, such non-reference systems not only are simpler than the reference kind, but also require less storage capacity.

The present invention is directed particularly to such "non-reference/local" systems.

Known inspection systems of the non-reference type use either dimensional verification (gauging) or pattern recognition to determine consistency between the article under test and the design rules or characteristics. A system using dimensional verification is disclosed in the aforementioned paper by R. C. Restrick and involves detecting successive edges of either the same line, or adjacent lines, and gauging the distance between them. A defect is signalled if this distance is wrong when compared with the design rules. Dimensional verification systems can readily detect pinholes in, or excess material between, interconnection conductors because the edges of the pinhole or excess material occur within the prescribed minimum distance between the aforementioned successive edges. They are not entirely satisfactory, however, for detecting pinholes in large areas such as ground planes or, conversely, small conductive blemishes in large substrate areas. It is, of course, desirable to detect such defects, if only because they imply poor quality control.

The alternative non-reference technique, pattern recognition, primarily involves watching for irregularities in the shape of an edge. This may involve "tracking" the edge, for example, as disclosed by P. E. Danielson and B. Kruse in a paper entitled "Distance Checking Algorithms", Computer Graphics and Image Processing, Vol. 11, pp. 349–376, 1979, or by template matching, for example as disclosed by J. F. Jarvis in a paper entitled "A Method for Automating the Visual Inspection of Printed Wiring Boards", I.E.E.E. Transactions on Pattern Analysis and Machine Intelligence, Vol. PAMI-2, No. 1, January 1980. Such known pattern recognition techniques are generally adequate for detecting small, abrupt changes, but not suitable for detecting locally-consistent defects, such as a gradual narrowing of a conductor. Also they might not detect a complete cut or bridging if it is regular after digitization and follows the design rules.

An object of the present invention is to eliminate, or at least mitigate the aforementioned problem of the non-reference kind of inspection system. To this end, according to one aspect of the present invention, there is provided an automatic inspection system of the non-reference kind wherein both dimensional verification and pattern recognition are employed.

According to one aspect of the invention, apparatus for automatically inspecting a patterned article comprises:

(i) image acquisition means for acquiring an image of at least part of said article and providing a binary signal, each bit of such binary signal representing a picture element of said image;

(ii) means for storing temporarily a number of bits of said binary signal;

(iii) means for accessing the stored bits and determining the logical states of two sets of such bits;

one set comprising at least one pair of bits corresponding, in said image, to a respective pair of picture elements that are spaced apart by a distance equivalent to the spacing between successive line edges of the pattern on said patterned article;

the other set comprising a plurality of bits corresponding, in said image, to a predetermined array of picture elements;

(iv) dimensional verification means responsive to the means for accessing the stored bits for providing a dimensional verification fault signal in dependence upon whether or not the states of said one set of bits indicate that successive line edges are said predetermined dimension apart;

(v) edge detection means esponsive to the means for accessing the stored bits for providing, in dependence upon the states of a plurality of bits of said other set, an edge signal indicating that said array of adjacent picture elements straddles an edge between contrasting areas of said pattern;

(vi) storage means for a set of templates, each representing an acceptable edge profile;

(vii) pattern recognition means responsive to the state of said other set of bits and to said edge signal for providing a pattern recognition fault signal indicating whether or not the pattern formed by said array of picture elements corresponds to an acceptable edge profile; and (viii) output means responsive to said dimensional verification means and said pattern recognition means for providing a fault signal indication.

The means for accessing the stored bits may be tapped delay means arranged so that the taps form a matrix or "window" corresponding to a relatively small portion of the area of the image, the "window" being arranged to scan the image as the binary signal passes through the tapped delay means.

Preferably, the output means is arranged to collate or "cluster" a plurality of outputs from the DV and PR means, determine whether they are so spatially grouped as to imply the presence of a true defect and, if so, signal a defect. To take into account that the outputs of the dimensional verification means and pattern recognition means, respectively, will have a different probability of representing a true fault, the outputs of the dimensional verification means and pattern recognition means may be weighted and a defect indicated when either individually or in combination, they reach a predetermined number. For example, if, as is likely, the DV means output is more probably correct than the PR means, a defect may be signalled either for a single DV defect indication or for a plurality of spatially neighbouring PR indications.

The said one and said other set of picture elements/bits are preferably, but not necessarily, mutually exclusive. The second set (PR) may be circumscribed by the first set (DV).

Preferably the two sets of elements have one in common, serving as a datum for DV and PR measurements. Then the respective DV and PR outputs, especially when "cluseered", will not need to be offset relative to each other. The one or outer set may be configured in dependence upon the expected orientations of the lines making up the pattern. For example, the points may be disposed about an approximation to a circle. One element may be at the centre of the circle and serve to determine whether the pair of elements/bits under consideration straddles a conductor/line or a space between lines. This centre element may be the common picture element (or tap) for both DV and PR sets of elements. The remaining elements may then be located in diametrically opposite pairs located at 45° intervals. Such an arrangement is particularly suited to articles having patterns laid out by computer-aided design (CAD), with lines or conductors horizontal, vertical or oblique. The diameter of the circle will be determined in dependence upon the edge spacings of lines or conductors in the image of the particular article to be tested.

A second ring of elements, similarly disposed but closer to the datum than the first ring may be provided. The diametrical spacings of the different ring sets may then correspond to line spacing and line width, respectively. The condition of the centre element may then be used in selecting whether to carry out a spacing check on the appropriate ring of elements or a line width check on the other ring.

The said other set of elements, i.e. that used for pattern recognition, may comprise a rectangular array. This is preferred for rectilinear edges. An oblong array might be preferred if lines were predominantly in one direction.

An embodiment of the invention will now be described, by way of example only, with reference to the accompanying drawings, in which.

Figure 1:
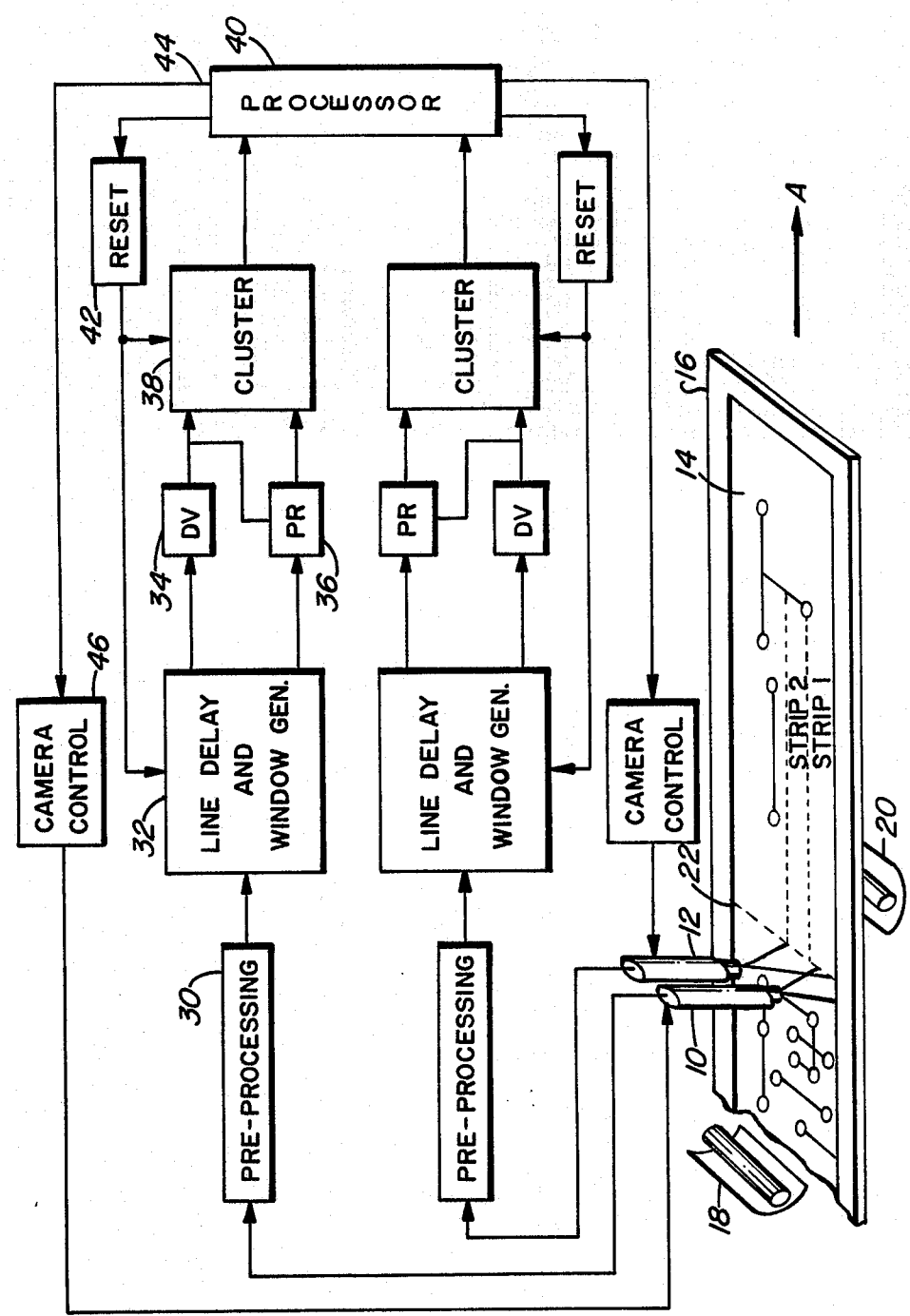
FIG. 1 is a schematic representation of an optical printed circuit board inspection system.

Referring to FIG. 1, a printed circuit board (PCB) inspection system comprises image acquisition means in the form of two cameras 10 and 12, respectively. The cameras are mounted above, and aimed at, the uppermost surface of a printed circuit board (PCB) 14 supported by a table 16. The table 16 is movable to and fro in the direction of arrow A by suitable drive means (not shown) which may be of conventional construction.

Also, a translation mechanism (not shown) is provided to displace the cameras 10 and 12 and the circuit board 14 relative to each other in a direction transverse to the arrow A. The translation mechanism is actuated between each longitudinal scan of the circuit board 14, so that the entire width of the circuit board 14 is scanned in a series of parallel strips.

Although two cameras are shown, one or more could be used, with appropriate adjustment of the translation mechanism. If desired, a row of cameras could span the entire width of the circuit board, in which case the translation mechanism would not be needed.

A light source 18, positioned above the table 16, irradiates the uppermost surface of the PCB 14. A second light source 20, positioned beneath the table 16, irradiates the underside of the PCB 14 through slit 22 in the table 16. In the case of an opaque article, such as the PCB illustrated, the cameras 10 and 12 receive reflected light from the first source 18. In addition, they receive some transmitted light from second source 20, which reaches the cameras via any through-holes in the PCB. The intensity of the second light source 20 is such that the light transmitted through the holes will be the same intensity as the light reflected from the conductor pad surrounding the hole. Then the hole will appear "invisible" to the cameras. When the article transmits light, as in the case of a phototool or mask, light source 20 alone suffices.

The cameras 10 and 12 are positioned along, and directly above, the slit 22. Embodiments of the invention could store and process the entire image of a PCB or other article as a two-dimensional "snapshot". However, in view of the vast amounts of information that would be involved, it is preferred to use a line camera and scanning. Thus, each of the cameras 10 and 12 is a line camera, specifically a linear CCD array camera, arranged to view a strip of the PCB. Each strip comprises 2048 picture elements and is one inch wide @0.5 mil resolution or 2 inches wide @1 mil resolution. Adjacent strips overlap slightly, for example by about ten percent, to ensure complete coverage of the article.

(Other scanning arrangements are possible, of course, for example using an X-Y table.)

The image information signal from each camera is passed line-by-line to image analysing circuitry which determines the locations of apparent faults or defects. Since the circuitry is the same for both cameras, only that associated with camera 10 will be described.

The analogue output from camera 10 is applied to a signal preprocessor 30 which converts it into a binary signal for application to a line delay and window generator 32. In the window generator 32, consecutive lines of the image scan are stored and access is provided to a window comprising an array of 32×32 picture elements (pels). One predetermined set of these elements (a pair of concentric rings) is accessed by dimensional verification (DV) means 34, and a second set (a central rectangle) is accessed by pattern recognition (PR) means 36. The dimensional verification means 34 and pattern recognition means 36 determine, in a manner to be described later, the existence of an apparent fault or defect in the array of elements and supply corresponding DV fault signals and PR fault signals to the clustering means 38. The clustering means 38 clusters and weights the two signals and supplies the resulting data to a control processor 40, which signals the occurrence of a fault.

The processor 40 also controls, by way of reset signal means 42, the generatio of a reset signal for application to window generator 32 and clustering means 38, respectively. Also, by way of line 44, the processor 40 controls camera control means 46, which generates a clock signal and exposure control signal for application to camera 10.

Figure 2:
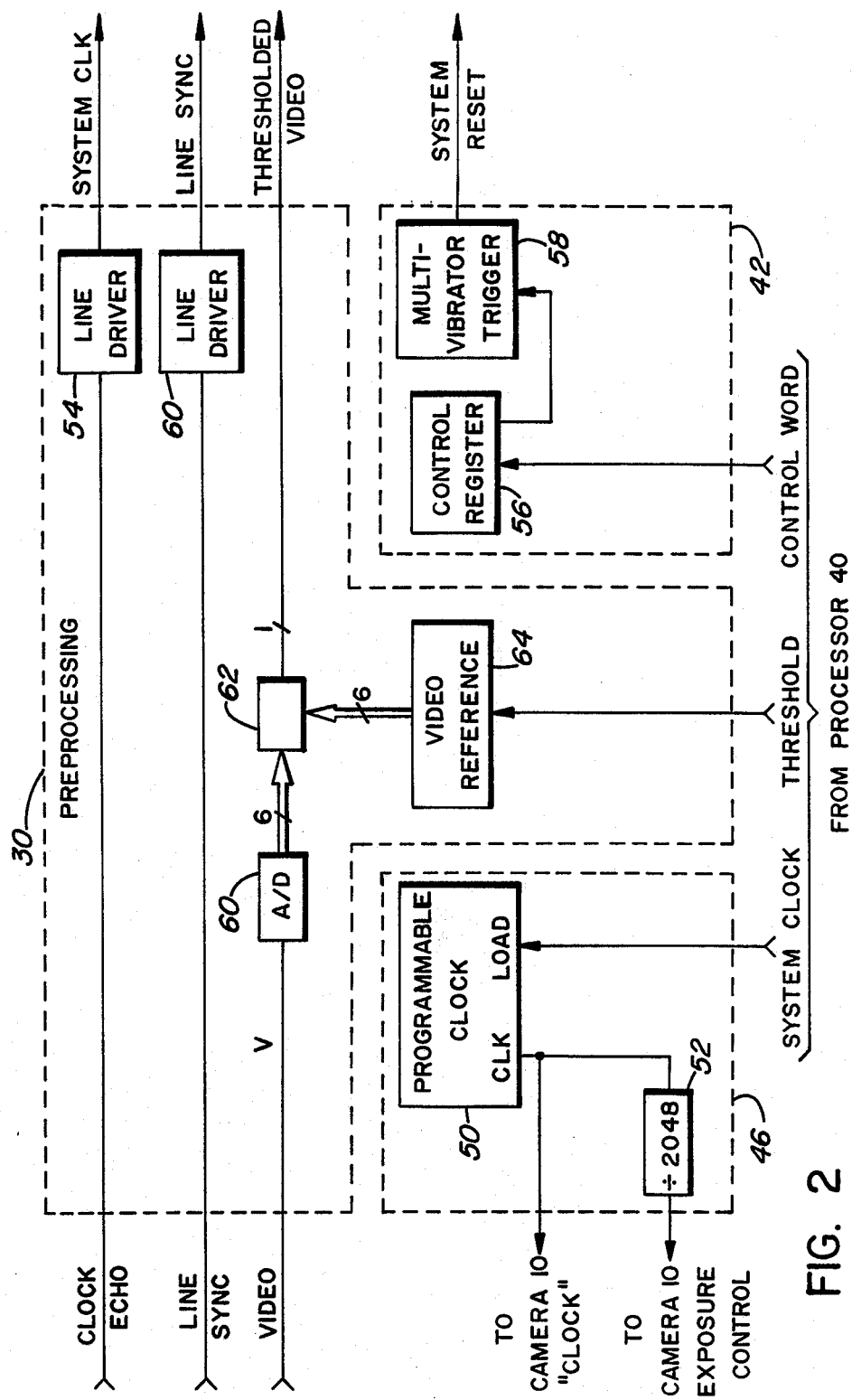
FIG. 2 is a block diagram of a pre-processing and camera control means of the system represented in FIG. 1.

For convenience, more detailed diagrams of the preprocessor 30, camera control 46 and reset signal means 42 are shown together in FIG. 2. The camera control means 46 comprises a programmable clock 50 which is loaded from processor 40. The 1 MHz clock signal, generated by programmable clock 50, is applied directly to the "clock" input of camera 10 and controls removal of data from the readout array of the camera 10. The output of the programmable clock 50 is divided by means of a divide-by-2048 device 52 and applied to the exposure control input of camera 10. This "exposure" control determines the transfer of integrated exposure charges from the integrating array to the readout array. This occurs every millisecond or 2048 pels. The clock echo signal from the camera 10 is applied to a line driver 54 and used as a system-wide clock.

The reset signal generating means 42 comprises a control register 56 to which is applied a control word from the processor 40. One bit of the output of control register 56 is applied to a multivibrator trigger 58 wiich generates therefrom the system reset signal a 1 millisecond pulse on a rising edge of the control bit. The output of control register 56 is used for other control functions, for example for selecting appropriate DV rings of elements.

In addition to line driver 54, which propagates the system clock, the preprocessing means 30 includes a line driver 60 for propagating the line sync output, for application to the window generator 32 and clustering means 38.

As previously mentioned, the preprocessing means 30 converts the analogue signal from the camera 10 into a bilevel digital signal. As shown in FIG. 2, the analogue signal from camera 10 is applied to an analogue/digital converter 60. The output of the A/D converter 60, which is a 6-bit word, is applied to a comparator 62, together with a 6-bit video reference signal generated by video reference means 64.

In the case of a PCB, the reference threshold is set so as to discriminate between the conductor material, which reflects incident light well, and substrate or insulator material, which reflects light to a lesser extent and so appears darker in the recorded images. In the case of a phototool, the reference threshold will be set to discriminate between substantially opaque and transparent parts of the phototool. A signal level of "1" represents conductor area of a PCB or opaque area of a phototool and a signal level of "0" represents substrate area of a PCB or transparent area of a phototool.

For phototools, the camera output signal may be quite clean, in which case a "fixed" threshold will usually be adequate. The conversion can then be implemented conveniently using an A/D converter followed by a comparator as illustrated. The video reference means 64 then comprises a 6-bit register written into by the processor 40.

In the specific embodiment, the threshold was determined using a mode-seeking method performed off-line. A number, e.g. 40, of images were pre-recorded and their global histogram analyzed. It had two prominent peaks with a valley in between. The midpoint of the valley was determined and the final threshold was set to correspond to the midpoint of the valley.

For good results with PCBs, an adaptive thresholding technique may be preferred. Then, instead of a 6-bit constant, the threshold would be a variable level generated by the video reference means 64 and adapted in accordance with local illumination and contrast parameters.

Figure 3:
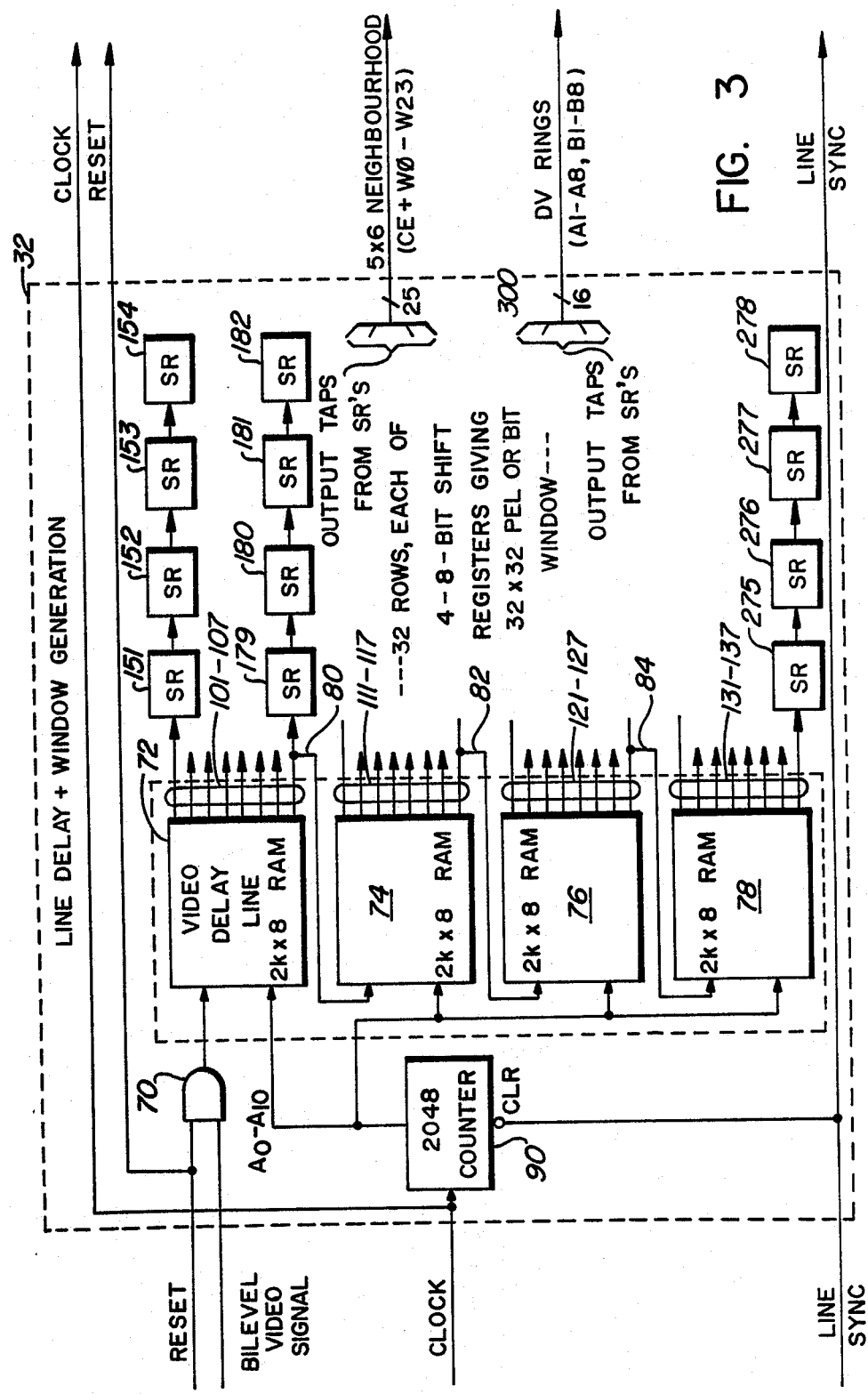
FIG. 3 is a block diagram of a line delay and window generation means of the system represented in FIG. 1.

Referring now to FIG. 3, the thresholded or bilevel signal from comparator 62 (FIG. 2) and the system reset signal from multivibrator 58 are supplied to window generator 32, which provides individual bit-access to a 32×32 bit (pel) window. As the video signal passes through the window generator, the window effectively scans the entire surface to be inspected.

At the input to the window generator 32, the bilevel video signal and reset signal are applied to respective inputs of an AND gate 70. The output of AND gate 70 is applied to the input of a fast random access memory (RAM) 72, which is connected in series with three more fast random access memories (RAMs) 74, 76 and 78, respectively. Each fast random access memory has storage for eight 2K lines. Therefore the four RAMs 72, 74, 76 and 78 serve as video delay lines and provide storage for 32 scan lines of image data, each line being 2048 picture elements (pels) wide. The AND gate 70 is used to zero the contents of the video delay lines at system reset, usually at the beginning of each strip of the scanning pattern.

The eighth or last data line of RAM 72 is connected to the first data line of RAM 74 as indicated by link 80. Likewise the last lines of RAMs 74 and 76 are connected to the first lines of RAMs 76 and 78, respectively, as indicated by corresponding links 82 and 84.

All four RAMs 72-78 are addressed by a 2048 counter 90, which is clocked by the system clock and cleared by the line sync. In operation, successive read/modify/write cycles read a previous image value from memory and store the next value. Each data line is cross-connected to the next, so a bit appearing at the end of the first line will be loaded into the beginning of the next line of the RAM. Thus, the image data passes serially through the four RAMs which serve as a long video delay line.

The "delay line" has 32 taps separated, in effect, by one line scan or 2048 pels. The taps are implemented using the 32 data output pins of the RAMs 72-78. In the diagram these data lines are numbered in four groups, vis. 101-107, 111-117, 121-127 and 131-137, respectively, and each data line is connected to the input of the first shift register in a row of four serially-connected 8-bit registers. The shift registers, numbered 151-278, are not all shown. Each shift register has eight accessible outputs or taps, one for each bit.

In opeaation, when a previous value from one line of a RAM is transferred to the next line of that RAM (or the next RAM), it is also read into the associated shift register. Thus, the image data passes through the bank of shift registers 151-278, with a delay between rows of one line scan (2048 pels) so that bits in the shift register have spatial positions correspnding to the points of the image to which they correspond.

As the image data passes through the shift registers, therefore, at each image point (clock cycle) a 32×32 element window is available at the taps of the shift registers.

Figure 7:
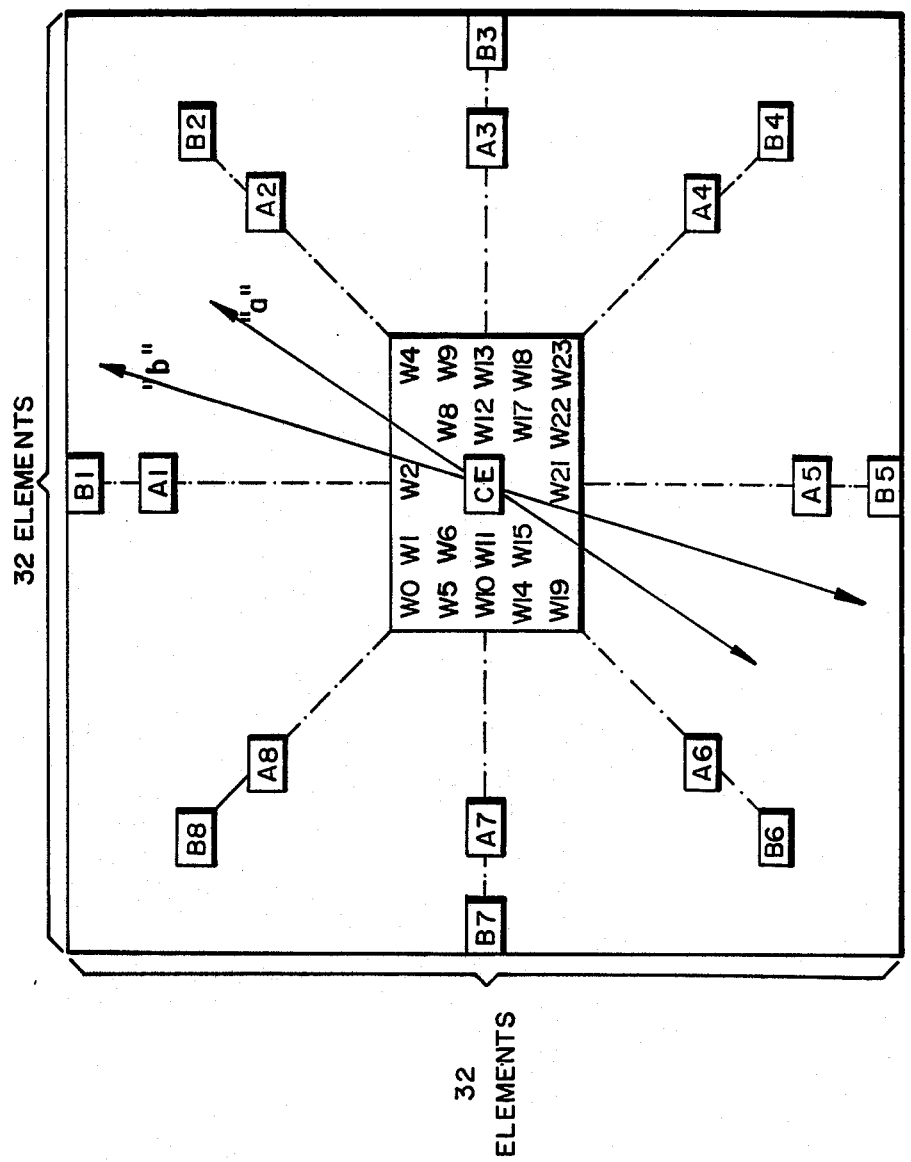
FIG. 7 is a diagram of the window or picture element array showing the elements used by the dimensional verification means and the pattern recognition means.

Two sets of elements of the window are actually accessed. The first set is accessed by way of line 300 by the dimensional verification means 34 and constitutes eight pels designated A1-A8 and eight designated B1-B8, together with a centre element CE. As shown in FIG. 7, elements A1-AB are arranged each equidistant from it neighbour in an approximately circular array of diameter a. Taking the horizontal direction in FIG. 7 as being the direction of line scan, elements A1 and A5 are diametrically opposed on the vertical axis and equidistant from the centre element CE. Elements A3 and A7 are similarly disposed along the horizontal axis, elements A2 and A6 along the +45° oblique axis and elements A4 and A8 along the −45° oblique axis.

Elements B1-B8 are radially aligned with elements A1-A8, respectively, but are further away from the centre element CE to lie on an approximate circle of diameter b.

The two circles of elements A1-A8 and B1-B8 constitute the first set of picture elements which are used for dimensional verification.

The circle diameters a and b correspond to minimum permissible conductor spacing and minimum permissible width, respectively. The condition of the centre element CE will determine whether a conductor width verification or a spacing verification is to be made. Thus, in the specific example, if the centre element CE is on substrate, a conductor spacing verification is performed on each pair of diametrically opposed elements and the pair of elements on the diameter that is perpendicular thereto. Then a minimum conductor spacing fault, i.e. conductor spacing less than minimum in any of the four orientations, is indicated if the centre element CE is on the substrate and A* $\overline{CE}$ is true where:

$$A = A1 * A5 * \overline{A3} * \overline{A7} +$$
$$A2 * A6 * \overline{A4} * \overline{A8} +$$
$$A3 * A7 * \overline{A5} * \overline{A1} +$$
$$A4 * A8 * \overline{A2} * \overline{A6}$$
(1)

where
 *=AND
 +=OR
 An=conductor
 $\overline{An}$=substrate

Similarly, a minimum conductor width flaw, i.e. the width of the conductor less than the prescribed minimum, will be indicated if, when the centre element CE is above conductor and B*CE is true, where:

$$B = B1 * B5 * \overline{B3} * \overline{B7} +$$
$$B2 * B6 * \overline{B4} * \overline{B8} +$$
$$B3 * B7 * \overline{B5} * \overline{B1} +$$
$$B4 * B8 * \overline{B2} * \overline{B6}$$
(2)

If either of these conditions occurs, the X-Y coordinates of the indicated flaw (the centre element CE) are transmitted to the clustering means 38.

Figure 4:
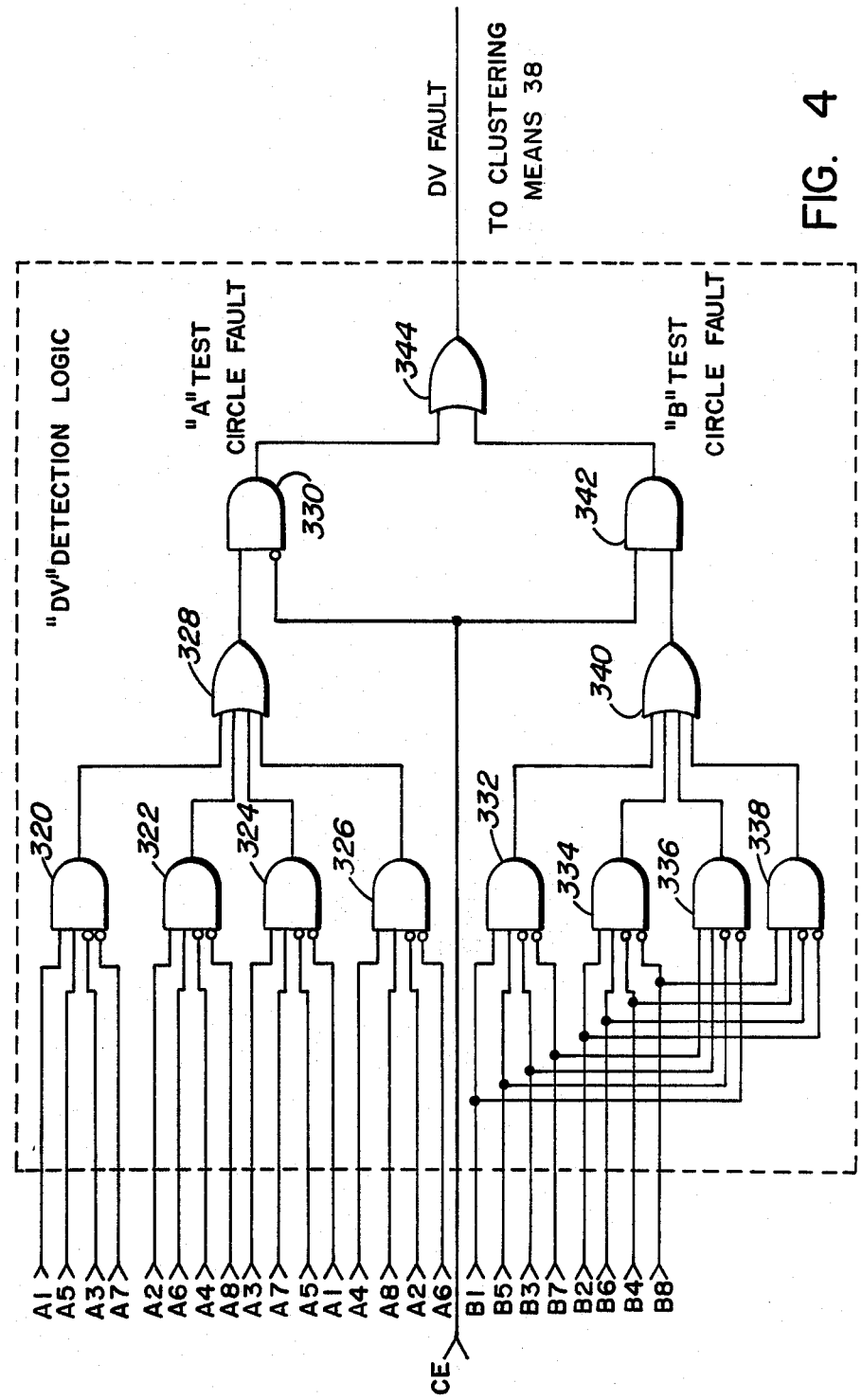
FIG. 4 is a schematic diagram of dimensional verification means of the system.

Implementation of the analysis of the condition of the DV elements is conveniently achieved by means of a logic array as shown in FIG. 4. Elements A1-A8 are applied in accordance with equation 1 above to the appropriate inputs of four AND gates 320, 322, 324 and 326, respectively, the outputs of which are applied to an OR gate 328. The output of OR gate 328 is applied to one input of an AND gate 330, which has an inverting input to which the value of centre element CE is applied.

The logic for processing elements B1-B8 is similar, comprising four AND gates 332, 334, 336 and 338, respectively, an OR gate 340 and an AND gate 342. However, in this case the centre element value CE is applied to the corresponding AND gate 342 without inversion (to enable the test only above conductor material).

The outputs of AND gates 330 and 342 are applid to an OR gate 344, the output of which indicates the presence of a dimensional verification violation of either kind and is fed to the clustering means 38 via the pattern recognition means 36.

In addition to the dimensional verification, if the centre element is at the edge of a conductor, a pattern recognition check is carried out. Only patterns of elements centered on an edge are examined because that is how PR-recognizable defects will manifest themselves in the binarized image. An edge point is defined as a point for which the centre element CE lies above a conductor and at least one of its four nearest neighbour pels is on substrate. Obviously, the edge could be detected by decreeing that when the centre element is on substrate at least one of its nearest neighbour pels is on conductor.

Elements not corresponding to an edge point are not examined. Once an edge has been detected in this way, the pattern recognition check is carried out on the 5×5 matrix of pels centered on the centre element CE (see FIG. 7). The sets of 5×5 elements are compared with successive ones of a set of templates representing valid patterns. If a match is found, the pattern or 5×5 matrix is deemed "good" and discarded, the next one then being compared. On the other hand, if the pattern is not found in the bank of valid patterns, a pattern recognition type of flaw is indicated.

Figure 5:
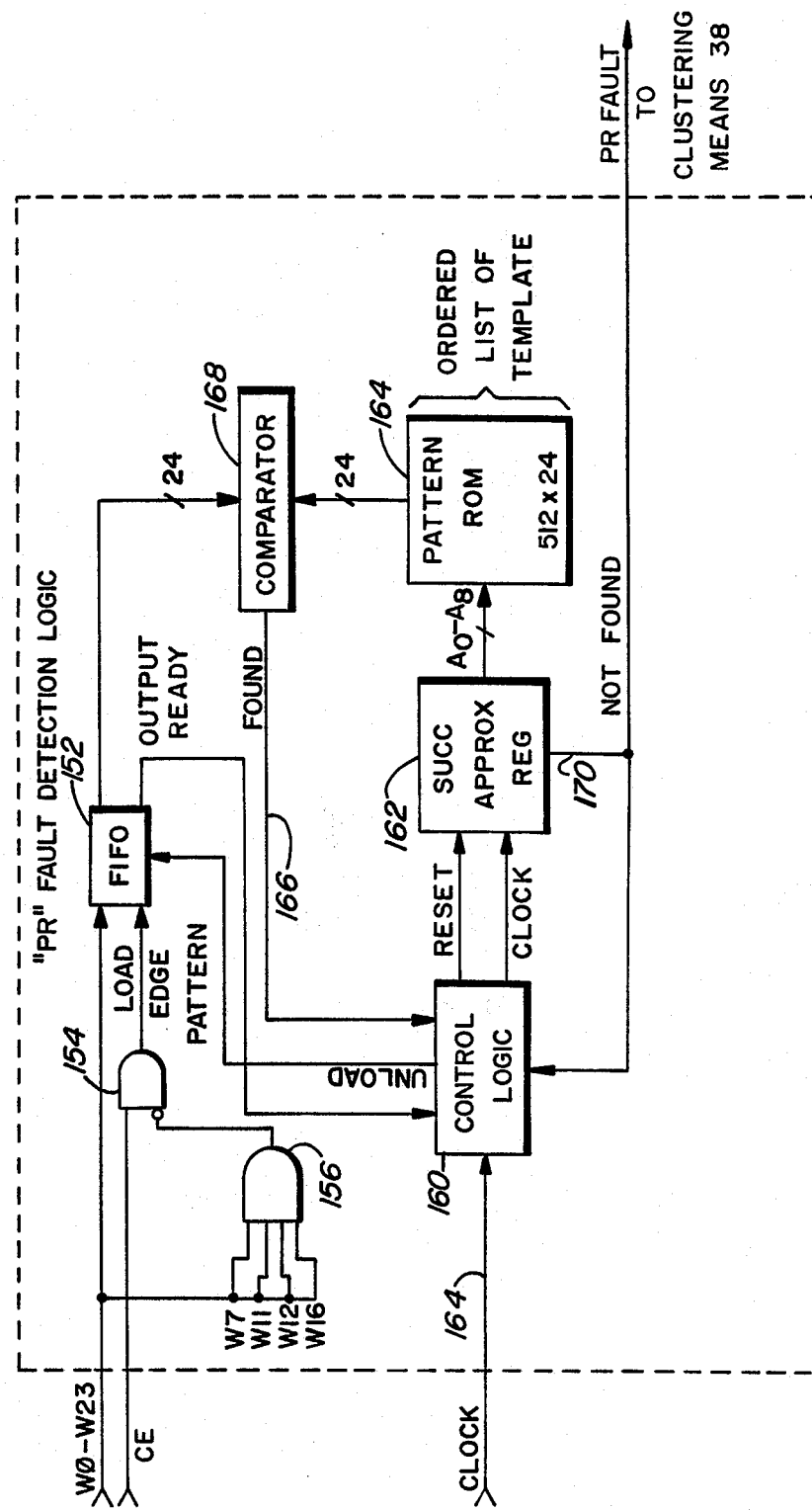
FIG. 5 is a block diagram of pattern recognition means of the system.

The pattern recognition procedure is conveniently implemented using the circuitry shown in FIG. 5.

Pattern recognition means 36 comprises a comparator 168, to which the elements W0-W23 of the 5×5 matrix are applied by way of a FIFO 152 which acts as a buffer (CE is not compared so only 24-bit words are required). The centre element CE is one input of an AND gate 154, the output of which is applied to the FIFO 152. The "nearest neighbour" elements, numbers W7, W11, W12 and W16 are applied to the four inputs of an AND gate 156, the output of which is applied, inverted, to the second input of AND gate 154. Thus, if the centre element CE is on conductor and any one of elements W7, W11, W12 and W16 is not, the output of gate 154 goes high, which causes the pattern of elements W0-W23 to be loaded into FIFO 152. It is not necessary for the centre element CE to be compared with the valid patterns since its state is already known, i.e. "1". The output of gate 154 represents the edge point signal. Once an edge is detected, several (up to 9) clock cycles are needed to compare the 24 element pattern with the templates (512). Only nine cycles are needed using successive approximation, i.e. cutting the range in half each time the comparison is made.

The corresponding output of FIFO 152 is applied to control logic 160, which controls reset and clock functions of successive approximations register 162. The control logic 160 derives its clock signal from the system clock on line 164 and receives a "found" signal via line 166 from a comparator 168. The successive approximations register 162 generates addresses $A_0$-$A_8$ for a read-only memory 164 (conveniently three EPROMS). These EPROMS 164 contain the list of valid patterns arranged in increasing order of magnitude, i.e. the 24-bit templates are arranged in such an order that, if they were interpreted as unsigned integers, they would be increasing in magnitude. In the specific example, the EPROM 164 contains 512 templates, each comprising 24 elements. The EPROMs 164 are connected to the comparator 168, together with the 24-bit output of FIFO 152. Thus, the templates can be compared, in turn, with the 24 elements W0-W23 of the 5×5 matrix in question. The comparator 168 is coupled via line 164 to the reset input of successive approximation register 160. If a match is found between the pattern in question and one of the valid templates, the successive approximations register 162 is reset via line 164 from the comparator 168. The pattern under test is therefore a valid pattern, so it is discarded in response to an unload signal to FIFO 152 from control logic block 160, via the "unload" line. A new edge pattern is then applied to the comparator 68, by the FIFO 152, and the comparison process repeated. The successive approximations register 162 starts with the mid-point address of the EPROM 164. The comparator 168 signals whether the "unknown" is greater than, equal to, or less than the mid-point template. The register 162 selects the mid-point of the appropriate half and the process repeats. If no match has been found and all nine cycles have been used, the successive approximation register signals "no match" on line 170, i.e. an apparent PR fault, and signals the control logic 160 to unload the pattern.

The "no match" output 170 of register 162, which is actually the 10th bit (A9) of the successive approximations register (assuming 512 templates) is also applied to one input of an OR gate 172 (see FIG. 6), the other input of which receives the DV fault signal from dimensional verification means 34. The output of OR gate 172 on line 176 is applied to the clustering means 38, shown in more detail in FIG. 6

As mentioned previously, the clustering means 38 serves to cluster and weight the "fault" signals from the dimensional verification means 34 and the pattern recognition means 36, respectively. Thus, the circuit accumulates the DV and PR faults detected and assigns a relative weight or degree of confidence to them.

Figure 6:
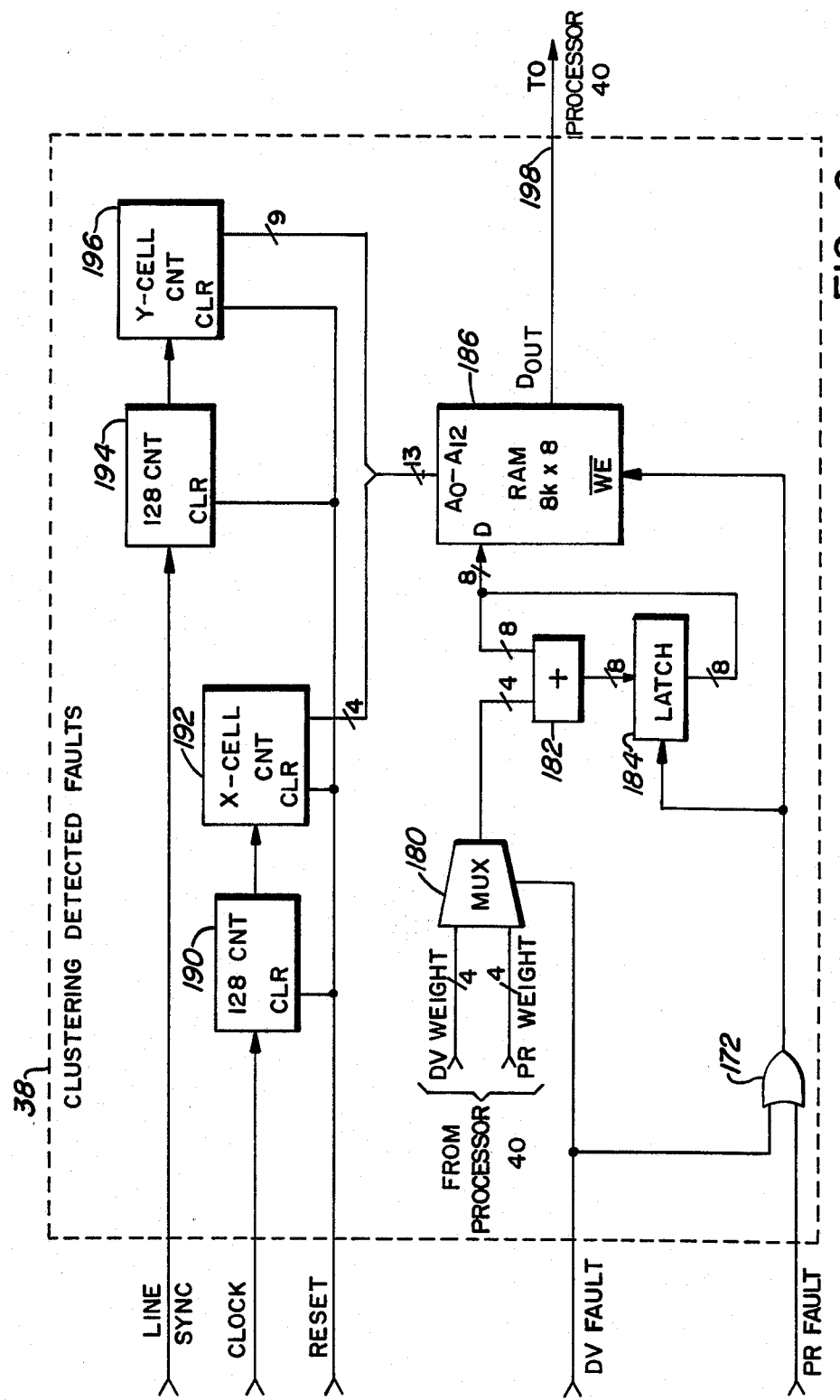
FIG. 6 is a block diagram of clustering means for clustering the outputs of the dimensional verification means and pattern recognition means of FIGS. 4 and 5, respectively.

Referring to FIG. 6, the relative weights of the DV and PR faults are applied to respective inputs of a multiplexer 180. Switching of the multiplexer 180 is controlled by the output signal from OR gate 172 in the pattern recognition means 36 (see FIG. 5). The 4-bit output of the multiplexer 180 is applied to one input of summing means 182. The output of summing means 182 is latched by latch 84. The 8-bit output of latch 184 is applied to the second input of summing means 182 and to the input of a 8K×8 random access memory (RAM) 186. When a DV or PR fault is detected, the appropriate weight (a 4-bit integer selected by MUX 180) is accumulated by the latch 184 and summer 182. The function of the latch 184 and summing means 182 is to accumulate weighted PR and DV faults for individual cells or discrete areas of the printed circuit board being scanned.

Figure 8:
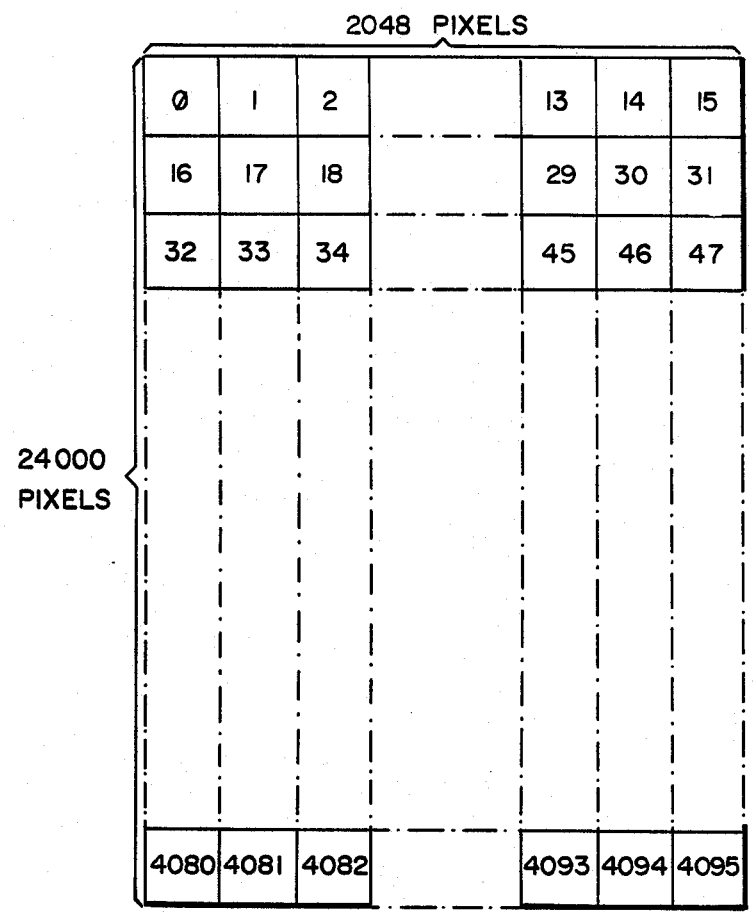
FIG. 8 is a representation of the cell-partitioning of the surface being scanned.

The strip being inspected is divided into cells each 128×128 pixels, as illustrated in FIG. 8. Such division is performed by four counters 190, 192, 194 and 196. Counter 190 is a 128-pixel counter clocked by the system clock and reset by the reset signal. Its output is applied to counter 192 which counts the number of such cells in the "X" or line scan direction, which in the specific example comprises 2048 pixels, or 16 cells.

Counter 194 is clocked by the line sync signal from the camera via line driver 60 (FIG. 2) and reset by the reset signal. It counts the number of lines in the "Y" direction or PCB travel direction up to a maximum of 128 lines. Its output is applied to counter 196 which counts the number of 128-line cells in the "Y" direction i.e. along the length of the PCB. Typically this is the 24 inch dimension of the usual 18 inch×24 inch board and is equal to 24,000 pels or 190 cells at 1 mil resolution. Thus each strip scanned in one pass by the respective camera comprises 2048×24,000 pixels (@0.001 inch resolution) or 16×190 cells. The outputs of X-cell counter 192 and Y-cell counter 196, respectively, are applied to the address input of RAM 186. They provide the address of each cell for which PR/DV fault indications or "counts" are being accumulated in RAM 186.

Thus, in operation of the clustering means 38, the counters 190-196 generate cell addresses for the RAM 186 and keep a running record of to which cell the current centre element (CE) belongs. When a DV or PR fault is found, its corresponding "weight" is added to the count at the appropriate location in the RAM 186. Providing that the RAM 186 has been cleared at the outset, when the entire strip of the PCB has been scanned, the total weight or score for each cell will be stored in the RAM 186. The contents of the RAM 186, outputted to the host processor 40 on line 198, can be read by the processor 40, which checks the "scores" of the different cells and notifies the operator of any cells with an excessive "score".

The weighting of the DV and PR fault indications can be done conveniently by a data multiplexer 180. The relative contributions will need to be selected according to the article being inspected. In practical embodiments for inspecting 18 inch×24 inch CAD-produced PCBs, relative contribution of 4 or 5 PR faults to 1 DV fault was satisfactory. Thus, every DV fault was multiplied five times before being entered into the RAM 186 (giving it more importance). Thus, if the 4-bit inputs to MUX 180 are 001(1) for PR and 0101(5) for DV, then five near PR faults will be equivalent to a single DV fault.

Instead of clustering fault indications in cells, the clustering means and processor may cluster on an individual basis. Then each individual "fault" location is stored and a search made for fault indications in neighbouring locations. If a predetermined number of such faults are found within a predetermined radius (hence a cluster), they are deemed to indicate a true defect.

Figure 9:
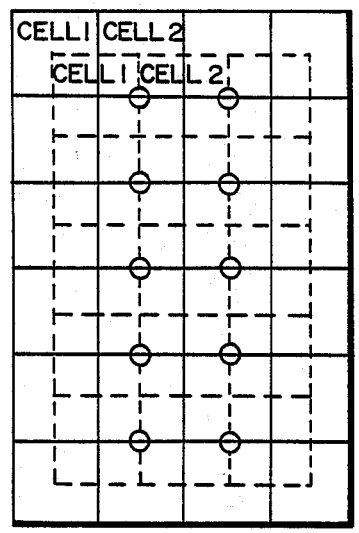
FIG. 9 represents a modified partitioning scheme with overlapping cell arrays.

A potential problem in cell-partitioning is that clusters occurring at the boundary of a cell may be divided into different cells. In such a case, the individual cells concerned might not have enough fault indications to initiate a defect report by the processor 40. The problem may be resolved by generating slightly overlapping cell arrays as illustrated in FIG. 9. The overlap illustrated is one half of the cell size in each direction. Possible ambiguities are then limited to the circled points which are where the boundary between two cells in one array intersects the boundary between two cells in the other array. If elimination of these potential ambiguities is desired, a third array of cells may be provided.

To implement these modifications requires, for each additional cell array, extra random access memory and counters for the appropriate cell sizes and offsets.

Various other modifications are comprehended by the present invention. Thus the image-acquisition process could be carried out by a laser scanner rather than the cameras and conventional light sources described herein.

Also, rather than have a plurality of cameas and one or more passes of the PCB in the same direction, a single camera might be provided and the camera and PCB moved relative to each other to scan the entire area. The positioning of these elements is particularly suited to testing PCBs which are laid out using, for example, computer-aided design. Generally such PCBs (and hence spaces therebetween) tending to have only four possible orientations, vis. longitudinal, lateral and both oblique directions. The dimensions will be determined by the particular artwork. If the minimum conductor width is euual to the minimum spacing only once circle need be used. Conversely, if more dimensions are to be monitored, additional circles may be provided.

Where the elements used for dimensional verification comprise two or more groups, they need not have the same reference or datum element (the centre element CE in the specific example). Likewise, the set of elements used for dimensional verification need not have the same datum as the set of elements used for pattern recognition. However, if different datums are used, the clustering means will need to account for any offsets.

It will be appreciated that the described configuration of the dimensional verification set of elements is suited to PCBs laid out using CAD rules, which specify that the conductors be horizontal, vertical, or at 45° (oblique) thereto. Accordingly, for other layouts a different configuration might be used.

It is also envisaged that clustering might be done by the processor, using a software module, rather than the circuitry described herein.

What is claimed is:

1. Apparatus for inspecting a patterned article, comprising:
   (i) image acquisition means for acquiring an image of at least part of said article and providing a binary signal, each bit of such binary signal representing a picture element of said image;
   (ii) storage means for storing bits of said binary signal, temporarily and successively;
   (iii) first means responsive to said storage means for determining the binary state of a first set of bits stored in said storage means, such first set corresponding, in said image, to at least one pair of picture elements that are spaced apart by a distance equivalent to the required spacing between successive edges between contrasting areas of the pattern on said article;
   (iv) dimensional verification means responsive to said first means for providing, in dependence upon the state of said pair of bits, a dimensional verification signal indicating whether or not said pair of picture elements are the required distance apart;
   (v) second means responsive to the storage means for determining, at the same instant, the state of a second set of bits corresponding, in said image, to a predetermined array of picture elements;
   (vi) pattern recognition means comprising edge detection means for determining whether or not said predetermined array of picture elements straddles an edge between contrasting areas of said pattern;
   means for storing a plurality of templates, each comprising an array of elements that represents an acceptable contour for such edge between contrasting areas, and
   means for comparing said second set of bits with said templates, said means for comparing being activated only upon detection of an edge by said edge detection means;
   said means for comparing providing a pattern recognition signal indicating whether or not the pattern formed by said array of picture elements, at a particular instant, corresponds to an acceptable edge profile; and
   (vii) output means responsive to said dimensional verification signal and said pattern recognition signal, for providing an output signal.

2. Apparatus as defined in claim 1, wherein said output means includes weighting means for weighting the dimensional verification signal and the pattern recognition signal, relative to one another, said output signal being generated when a plurality of fault indications have been accumulated.

3. Apparatus as defined in claim 2, wherein said weighting means serves to weight said signals such that determination of a fault location requires a greater number of pattern recognition fault indications than of dimensional verification fault indications.

4. Apparatus as defined in claim 3, wherein the weighting is in the ratio of 4 or 5 or 1.

5. Apparatus as defined in claim 1, wherein said output means includes:
   cell means for sub-dividing said image into a plurality of contiguous cells; and clustering means for accumulating successive fault-indicative outputs of said dimensional verification means and of said pattern recognition means, respectively, and cluster detection means for detecting the occurrence of a plurality of such fault-indicative outputs within a predetermined cell of said image and determining such to be said location of a defect.

6. Apparatus as defined in claim 5, wherein said output means includes weighting means for weighting the dimensional verification signal and the pattern recognition signal, respectively, relative to one another, said output signal being generated when a plurality of fault indications have been accumulated.

7. Apparatus as defined in claim 6, wherein said weighting means serves to weight said signals such that determination of a fault location requires a greater number of pattern recognition fault indications than of dimensional verification fault indications.

8. Apparatus as defined in claim 7, wherein the weighting is in the ratio of 4 or 5 to 1.

9. Apparatus as defined in claim 5, wherein said clustering means comprises:
a multiplexer for multiplexing the outputs of the dimensional verification means and pattern recognition means, respectively;
memory means for storing the output of said multiplexer; and
said cell means comprises means for addressing said memory so as to locate each fault-indicative output of said multiplexer in one of said plurality of cells.

10. Apparatus as defined in claim 9, wherein said image acquisition means comprises:
means for scanning said article line-by-line and said means for addressing comprises a counter responsive to a timing signal corresponding to the bit rate to determine the width of each cell in the X direction and a second counter responsive to a line-sync signal for determining the dimension of each cell in the Y direction.

11. Apparatus as defined in claim 10, wherein said counters comprise:
a first counter responsive to clock pulses for counting up to a number corresponding to the width of said cell;
a second counter responsive to the overflow output of said first counter for counting the number of cells across the width of the area of the image;
a third counter responsive to said line-sync signal for counting the number of picture elements in the height of the cell; and
a fourth counter responsive to the overflow output of the third counter for connting the number of cells along the length of the image.

12. Apparatus as defined in claim 1, wherein said dimensional verification means is responsive to a first set of bits corresponding to a plurality of pairs of picture elements, the elements of each pair being diametrically opposite about, and equidistant from, a datum.

13. Apparatus as defined in claim 1, wherein the first set of elements comprises at least two groups each of at least one pair of elements diametrically opposed about a common datum, the spacing between the pair of elements of one group being different from the spacing between the pair of elements of the other group and corresponding to a different spacing between edges of the pattern.

14. Apparatus as defined in claim 13, wherein said two groups each comprise a plurality of said pairs of elements, each such pair on a different diameter through said common centre element.

15. Apparatus as defined in claim 14, wherein each said pair of elements in one group lies on the same diameter as a pair of elements in the other group.

16. Apparatus as defined in claim 13, wherein said dimensional verification means further comprises means for determining the state of a bit corresponding to a picture element between the first-mentioned pair of elements and, in dependence thereupon, selecting one or other of said groups for determining the presence of a dimensional verification fault indication.

17. Apparatus as defined in claim 12, 13 or 16, comprising a first pair of elements on a first diameter, a second pair of elements on a diameter perpendicular to the first diameter, and two further pairs on the two oblique diameters, respectively.

18. Apparatus as defined in claim 1, wherein said edge detection means is responsive to a centre element of said array, and elements superjacent, subjacent, and juxtaposed about said centre element, in determining whether or not said array straddles said edge.

19. Apparatus as defined in claim 14, wherein said centre element corresponds to a datum element of the set of elements used by the dimensional verification means.

20. A method of inspecting a patterned article, comprising the steps of:
(i) acquiring an image of at least part of said article and providing a binary signal, each bit of such binary signal representing a picture element of said image;
(ii) storing bits of said binary signal, temporarily and successively;
(iii) responsive to the stored bits, determining the binary state of a first set of bits stored in said storage means, such first set corresponding, in said image, to at least one pair of picture elements that are spaced apart by a distance equivalent to the required spacing between successive edges between contrasting areas of the pattern on said article;
(iv) in dependence upon the state of said set of bits, providing a dimensional verification signal indicating whether or not said pair of picture elements are the required distance apart;
(v) responsive to the contents of said storage means, determining, at the same instant, the state of a second set of bits corresponding, in said image, to a predetermined array of picture elements;
(vi) determining whether or not said predetermined array of picture elements straddles an edge between contrasting areas of said pattern;
(vii) storing a plurality of templates, each comprising an array of elements that represents an acceptable contour for such edge between contrasting areas; comparing said second set of bits with said templates upon recognition of an edge between contrasting areas of said pattern, and
providing a pattern recognition signal indicating whether or not the pattern formed by said array of picture elements, at a particular instant, corresponds to an acceptable edge profile; and
(viii) responsive to said dimensional verification signal and said pattern recognition signal, providing an output signal.

21. A method as defined in claim 20, including the step of weighting the dimensional verification signal and the pattern recognition signal relative to one another.

22. A method as defined in claim 21, wherein said weighting serves to weight said signals such that determination of a fault location requires a greater number of pattern recognition fault indications than of dimensional verification fault indications.

23. A method as defined in claim 22, wherein the weighting is the the ratio of 4 or 5 to 1.

24. A method as defined in claim 20, including the step of sub-dividing said image into a plurality of contiguous cells, accumulating successive fault-indicative outputs of said dimensional verification means and of said pattern recognition means, respectively, and detecting the occurrence of a plurality of such fault-indicative outputs within a predetermined cell of said image and determining such to be said location of a defect.

25. A method as defined in claim 24, wherein said clustering includes the steps of multiplexing the outputs of the dimensional verification means and pattern recognition means, respectively, storing the product of said multiplexing in a memory, and addressing said memory so as to locate fault-indicative output of said multiplexer in one of said plurality of cells.

26. A method as defined in claim 25, wherein the step of acquiring an image comprises scanning said article line-by-line and said addressing of said memory is responsive to a timing signal corresponding to the bit rate to determine the width of each cell in the X direction and responsive to a line-sync signal for determining the dimension of each cell in the Y direction.

27. A method as defined in claim 26, wherein said addressing is by means of:
  a first counter responsive to clock pulses for counting up to a number corresponding to the width of said cell;
  a second counter responsive to the overflow output of said first counter for counting the number of cells across the width of the area of the image;
  a third counter responsive to said line-sync signal for counting the number of picture elements in the height of the cell;
  a fourth counter responsive to the overflow output of the third counter for counting the number of cells along the length of the image.

28. A method as defined in claim 20, wherein said dimensional verification signal is determined in response to a first set of bits corresponding to a plurality of pairs of picture elements, the elements of each pair being diametrically opposite about, and equidistant from, a datum.

29. A method as defined in claim 20, wherein the first set of elements comprises at least two groups each of at least one pair of elements diametrically opposed about a common datum, the spacing between the pair of elements of one group being different from the spacing between the pair of elements of the other group and corresponding to a different spacing between edges of the pattern.

30. A method as defined in claim 29, wherein each of said two groups comprises a plurality of pairs of elements, each such pair on a different diameter through said common centre element.

31. A method as defined in claim 30, wherein each said pair of elements in one group lies on the same diameter as a pair of elements in the other group.

32. A method as defined in claim 28, wherein said dimensional verification signal is provided by determining the state of a bit corresponding to a picture element between the first-mentioned pair of elements and, in dependence thereupon, selecting one or other of said groups for determining the presence of a dimensional verification fault indication.

33. A method as defined in claim 28, 29 or 32, wherein said set of picture elements comprises a first pair of elements on a first diameter, a second pair of elements on a diameter perpendicular to the first diameter, and two further pairs on the two oblique diameters, respectively.

34. A method as defined in claim 20 wherein detection of whether or not said array straddles an edge is by means of a centre element of said array, and elements superjacent, subjacent, and juxtaposed about said centre element.

35. A method as defined in claim 34, wherein said centre element corresponds to a datum element of the set of elements used by the dimensional verification means.

36. A method as defined in claim 20, including the step of weighting the dimensional verification signal and the pattern recognition signal relative to one another, said output signal being generated when a plurality of fault indications have been accumulated.

37. A method as defined in claim 36, wherein said weighting serves to weight said signals such that determination of a fault location requires a greater number of pattern recognition fault indications than of dimensional verification fault indications.

38. A method as defined in claim 37, wherein the weighting is in the ratio of 4 or 5 to 1.

* * * * *